United States Patent [19]

Gallop et al.

[11] Patent Number: 4,760,591
[45] Date of Patent: Jul. 26, 1988

[54] CEPHALOSTAT FOR CEPHALOMETRIC ROENTGENOGRAPHY

[75] Inventors: James Gallop, Wheaton; Andrew Majka, Chicago, both of Ill.

[73] Assignee: B. F. Wehmer Co., Inc., Franklin Park, Ill.

[21] Appl. No.: 865,250

[22] Filed: May 19, 1986

[51] Int. Cl.⁴ .............................................. G03B 42/02
[52] U.S. Cl. .................................... 378/170; 378/168; 378/169; 378/180
[58] Field of Search .............................. 378/168–169, 378/177, 179, 180, 208, 38–40

[56] References Cited

U.S. PATENT DOCUMENTS

| | | | |
|---|---|---|---|
| 2,032,833 | 3/1936 | Broadbent | 378/180 |
| 2,254,544 | 9/1941 | Plotz et al. | |
| 2,264,410 | 12/1941 | Schier | |
| 2,717,314 | 9/1955 | Delk, Sr. | |
| 2,846,587 | 8/1958 | Thurow | 378/180 |
| 3,072,788 | 1/1963 | Oller | |
| 3,154,683 | 10/1964 | Blair | |
| 3,293,430 | 12/1966 | Wustner | |
| 3,364,352 | 1/1968 | Fry et al. | |
| 3,514,606 | 5/1970 | Rabey | |
| 3,530,293 | 9/1970 | Wehmer | |
| 3,626,186 | 12/1971 | Allard | |
| 3,633,028 | 1/1972 | Marino | |
| 3,704,707 | 12/1972 | Halloran | |
| 3,737,660 | 6/1973 | Ando et al. | 378/180 |
| 3,790,803 | 2/1974 | Phillips | |
| 3,875,412 | 4/1975 | Hozumi | 378/208 |
| 3,916,207 | 10/1975 | Reed | |
| 4,088,893 | 5/1978 | Schroeder | 378/180 |
| 4,144,460 | 3/1979 | Norman | |
| 4,145,611 | 3/1979 | Valila | |
| 4,229,656 | 10/1980 | Iversen et al. | |
| 4,256,112 | 3/1981 | Kopf et al. | |
| 4,341,220 | 7/1982 | Perry | |
| 4,400,826 | 8/1983 | Preti et al. | |
| 4,566,444 | 1/1986 | Spolyar | |

FOREIGN PATENT DOCUMENTS 0587926 1/1978 U.S.S.R. ............................. 378/180

OTHER PUBLICATIONS

Brochure entitled "The Axialtome" (two pages) by Wilson Radiographic Systems, Inc.

Primary Examiner—Craig E. Church
Assistant Examiner—John C. Freeman
Attorney, Agent, or Firm—Lee & Smith

[57] ABSTRACT

An improved cephalostat comprising an upper housing portion and rotatable lower housing portion wherein a patient's head may be positioned below the lower housing portion and lateral, anterior, posterior, or frontal oblique, x-ray pictures may be selectively taken. Said lower housing portion includes a gear and gear rack assembly for the relative positioning of associated earposts and a top knob adjustment for the earposts extends outward from the top of the upper housing portion. The upper housing portion further accommodates adjustable support rod means for an x-ray cassette holder that is held laterally to one side of the upper housing portion. The lower housing portion is capable of accommodating support slide rods which carry a nasion positioner. The improved cephalostat further includes indexing holes through the top wall of the upper housing portion covered thereover by a rotatable index plate means having an index hole and pin whereby the pin may be selectively positioned into a chosen index hole of the top wall for locking the lower housing portion in a chosen rotational alignment. The cephalostat also includes a vertically and horizontally adjustable film cassette holder. The two housing portions are completely separable for maintenance and adjustment. The cephalostat may also include detachable supports for demountable attachment to a wall mounting plate.

24 Claims, 3 Drawing Sheets

CEPHALOSTAT FOR CEPHALOMETRIC ROENTGENOGRAPHY

BACKGROUND AND SUMMARY OF THE INVENTION

The invention is directed toward a cephalostat for positioning the patient between an x-ray tube and a film cassette so that cephalometric roentgenography may be accurately made and wherein sequential series of identical cephalometric views may be taken over time.

Cephalometric roentgenography of the type undertaken by dentists, and primarily those practicing orthodontistry, requires the utmost in precision and clarity as well as the rapid positioning of the patient with minimum inconvenience.

In order to accurately dispose the mid-sagital plane relative to the x-ray tube at a standard distance from the film, ear positioning posts are utilized in most cephalostat devices and include means for moving them relative to the patient in order that the skull is placed directly with the mid-sagital at a selected location. Additionally, a positioning of the Frankfort plane with respect to the horizontal is usually required to be made so that consistent, repetitive, sequential roentgenographic series may be taken. In conjunction with the positioning of the Frankfort plane and mid-sagital line, a nasion positioner is often provided. Also, to meet particular focusing, clarity and imaging requirements, the distance that the x-ray film cassette is disposed relative to the patient's head is preferably adjustable.

Usually, wall mounted x-ray tubes, supported by mechanical arms, are used in association with a fixator/collimator for accurate alignment limiting diffusion and minimizing the exposure area by the x-ray beam.

Cephalometric roentgenography is used by the general dentist although less frequently than by the more specialized orthodontist. A cephalostat that would serve the needs of both, and yet provide for precise positioning, clarity and minimum patient inconvenience, would be desirable.

In conjunction with serving the needs of both general and specialized use, it would also be desirable for the cephalostat to not only provide for taking the most common lateral cephalometric sequence, but also include the ability to position the patient for anterior and posterior exposures with the added benefit of being capable of positioning the patient for oblique pictures. In this regard, an adjustable mechanism for a cephalostat to selectively dispose the skull in said anterior, posterior, lateral and oblique arrangements, while consistently positioning the midsagital plane and Frankfort plane relative to the x-ray tube and film cassette, is highly preferred. An additional need in such a cephalostat device would be to provide for the demountability of the cephalostat from a wall mounting wherein efficient use of space in a dental office may be obtained when roentgenography is not required.

The ease with which a cephalostat is employed should include quick positioning of the patient with minimal inconvenience and apprehension. As a result, the movement of the earposts away from, and into contact with, the patient's ear canals, would be desirably accomplished with an easily accessible and very accurately-functioning adjustment means for moving the two earposts relative to each other.

In conjunction with the foregoing needs, it would be highly beneficial to provide for the variable movement of the nasion positioner inwardly and outwardly of the device to bring it closer to and away from the patient, as well as being able to vertically move a nose positioning flange into position at the bridge of the nose and then releasably lock in that position. Additionally, the housing means for such a cephalostat would also require that it include engagement means for attachment to supporting means on a wall. Also, it would be necessary that the housing means for the cephalostat accommodate an earpost adjustment mechanism, nasion adjustment mechanism, and further the ability to supportably accommodate cassette-holding tubes, or rods, for the positioning of an x-ray cassette holder at a selected distance from the mid-sagital plane.

Also, it would be desirable to provide an easily-used and simplified adjustable bracket means for the x-ray film cassette holder whereby to vertically move an x-ray film cassette relative to the patient's skull for accommodation of both children and adults, as well as the ability to hold an x-ray cassette, which is usually rectangular, either lengthwise or sideways.

Moreover, the movements and adjustments of the x-ray cassette holder, nasion positioning means, earposts means, and wall mounting engageable means, would necessarily involve a desirable combination with a rotational adjustment capability for the housing means whereby to position the patient's head in a range of angular positions relative to the x-ray tube whereby the earposts mechanism and nasion positioner move with one portion of the housing means, independently, and relatively to a separately supported film cassette holder in order to rotate the properly positioned skull at varying angles relative to the x-ray film held by the cassette holder.

All the foregoing adjustments must be made precisely, and quickly but yet be combined in a device which is compatible with a wide range of dental office arrangements and usable with existing wall mounted x-ray tube arm assemblies. These goals would also be preferably achieved by a device that is economically attractive and useful to almost all dental practitioners.

In accomplishing the foregoing objectives, it would also be desirable to provide a very compact cephalostat, having all the noted adjustment features, and in which simplified, but precise, adjustments can be made without the need for expensive and elaborate gearing and other adjustable mechanisms that could require extra repair and maintenance expenses in order to keep the devices in adjustment over time.

The present invention satisfies all the foregoing goals and objectives and provides a very compact, precise wall demountable cephalostat, having quick adjustment of an earpost mechanism, and the ability to angularly adjust a housing means whereby the patient's head may be placed at anterior, posterior, lateral, as well as oblique positions, relative to a separately adjustable and movable x-ray cassette holder. The invention also provides a double housing construction that permits one portion of the housing to be movable relative to the other whereby a nasion positioner and the earpost mechanisms may be moved to position the patient's head relative to a vertically and horizontally adjustable x-ray cassette holder that is mounted to a fixed housing portion of the cephalostat. The fixed portion of the housing means includes engageable means for attachment of support rods to be demountably engaged to a wall support plate means. Furthermore, the adjustment of the earpost mechanisms relative to the ear canals is manually achieved with an adjustment knob means located at the top of the fixed housing and arranged adjacent an adjustment means for the angular positioning of the second housing portion relative to the first, so that both adjustment means are thereby in close proximity for quick and precise use by the practitioner. In addition, an adjustment mechansim for a nasion positioner is provided with adjustment means conveniently located a short distance in front of the double housing means and wherein the fixed housing means also includes adjustable support means for sliding the cassette holder relative to the patient's head. The adjustable support means for the cassette holder is also in close convenient location to the nasion positioning adjustment, to the earpost adjustment means, and to the adjustable rotational positioning means for the double housing portions.

The invention may be summarized in part as comprising a wall-mounted cephalostat having a fixed upper, or first, housing portion mounted to rod means detachably supported at a wall plate means and a relatively movable second or lower housing portion rotatable relative to the first portion by a top-mounted adjustment knob means arranged on a shaft extending from the second housing portion to project upwardly and outwardly of the first housing. Further, a gear and rack means communicates with the lower end of the shaft interiorly of the second housing means. The gear and rack means are joined to two opposing earpost means and are able to move one relative to the other to firstly allow space under the housing means for the placement of the patient's head followed by the closure of the earpost means by oppositely rotating the adjustment knob means. The earpost means position the patient's head centrally below the bottom housing and at a consistent distance from the focal point of the x-ray tube that is wall mounted at a standard distance away from the cephalostat. The rotational adjustment of the second housing relative to the first housing is provided by an apertured index plate means rotably positioned atop the first housing and mounted with an upstanding hub of the second portion that extends through the first housing portion for supporting the second housing portion therethrough. Indexing holes are provided through a top wall of the first housing and a lock pin means is selectively insertable through the index plate means so that when the index aperture of the index plate means matches a hole on the top of the first housing, the pin means may be inserted to releasably lock the housings relative to each other in a desired relative angular positioning. A nasion positioner means is laterally positionable relative to the bottom housing means by the provision of slide rod means extending inwardly of the bottom, or second, housing but spaced to be out of the way of the gear and rack adjustment mechanism, and wherein a vertical nose slide for a nose bridge positioning portion includes a locking means for both the nose slide and slide rods whereby the nasion positioner may be jointly locked both laterally and vertically relative to the cephalostat housing portions. The first, or upper, housing body also includes cavity means, movably-accommodating slide rod means extending therethrough and supporting laterally thereof an adjustable, x-ray cassette holding means, in which an x-ray film cassette may be moved laterally and vertically relative to the housing body means. An engagement means is provided by the upper housing for engaging the ends of support rods that are connected at opposite ends to a wall mounting plate means, whereby the first housing supports the second housing, cassette holder means, earpost mechanism, and nasion positioner.

The first and second housing portions are compact but yet cooperate to provide several desirable adjustments, including: positioning of the gear rack by a top adjustment knob means for changing the earpost means position; slide rod means for moving the nasion positioner; slide rod means for moving the adjustable x-ray cassette holder; and, a pin and index plate means attached to the bottom housing hub and extending upwardly from the second through the first housing portion for the rotational adjustment of the second housing portion; whereby all may be adjusted in any sequence, or simultaneously, and without one impeding the adjustment of another. The relative positioning of the bottom housing to the top housing for anterior, posterior, lateral and frontal oblique roentgenography is further achieved by the placement therebetween of a lubricating pad means for aiding rotation relative therebetween. Similarly, the apertured index plate means, associated with an index pin means for indexing with holes in the top of the first body portion means, is rotatably carried by the second body portion hub means over the first body portion and includes lubrication therebetween for smooth rotation. The slide rod means facilitating the lateral motion of the x-ray cassette holder means, and the gear rack means facilitating the adjustment of the earposts, each include stop means whereby inadvertent disengagement from the housings is prevented. A unique simplified adjustment for the vertical positioning of an x-ray film cassette, and for accommodating the cassette lengthwise or sideways, is provided at the x-ray cassette holder means by virtue of two slots slidably engaged by opposing, preferably U-shaped, holders which are releasably secured by lock knob means, whereby the holders are vertically movable relative to each other by adjusting the lock knob means. An adjustment means of the nasion positioner makes possible the locking of the horizontal slide rod means by biasing the rod means against a friction fit bushing sleeve supportably extending inwardly of the second housing. The adjustment means serves the dual purpose of also locking a vertical nose slide member relative to the bridge of the patient's nose wherein both horizontal and vertical locking of the nasion positioner is achieved by one adjustment means. Additionally, the first and second housing body portions may be complementarily shaped to provide smooth, flush, outer exterior wall conformations with rounded corners, and wherein the bottom, or second housing, portion may be rotated relative to the first with allowance for rotational clearance of the nasion positioner around the first housing in order to expedite taking frontal oblique, anterior, posterior and lateral x-ray pictures in quick succession.

BRIEF DESCRIPTION OF THE DRAWINGS

FIG. 4 is a front view of the cephalostat as shown in FIG. 1, but at a larger scale to show greater detail thereof;

DETAILED DESCRIPTION OF THE PREFERRED EMBODIMENT FOR THE IMPROVED CEPHALOSTAT FOR ROENTGENOGRAPHY

With reference to the appended drawings, like reference numerals are used to refer to the same elements throughout.

Figure 1:
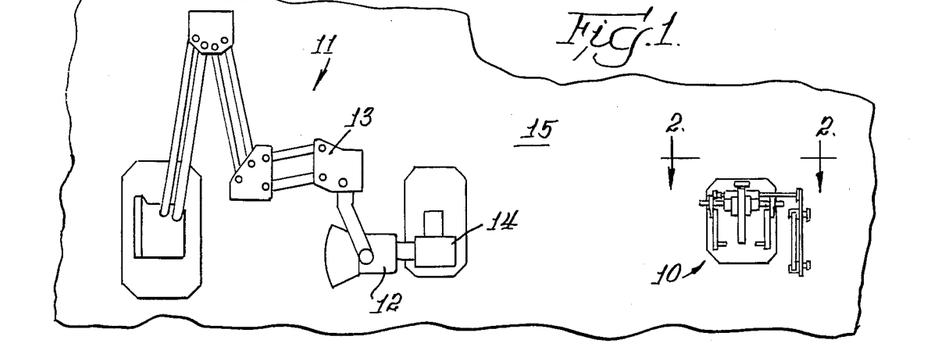
FIG. 1 is an elevational view of a wall mounted x-ray tube device, having the x-ray tube supported on an articulated arm in a known fashion, and being shown held at a fixator/collimator at a pre-selected distance from the inventive cephalostat shown mounted on the wall to the right thereof.

In FIG. 1, the improved cephalostat apparatus is generally referenced at numeral 10, to the right of an x-ray apparatus 11, having an x-ray tube 12 mounted on an articulated, swinging arm 13. The x-ray tube 12 is attached to a fixator/collimator 14 in a normal fashion whereby to provide focusing and to limit the diffusion of the x-ray. Both the cephalostat 10 and x-ray apparatus 11 are affixed to a wall 15 whereby the focal point of the x-ray tube is set to be a standardized distance of 60 inches from the mid-sagital plane of the skull when the patient is positioned at the cephalostat 10.

Figures 2, 7, 8:
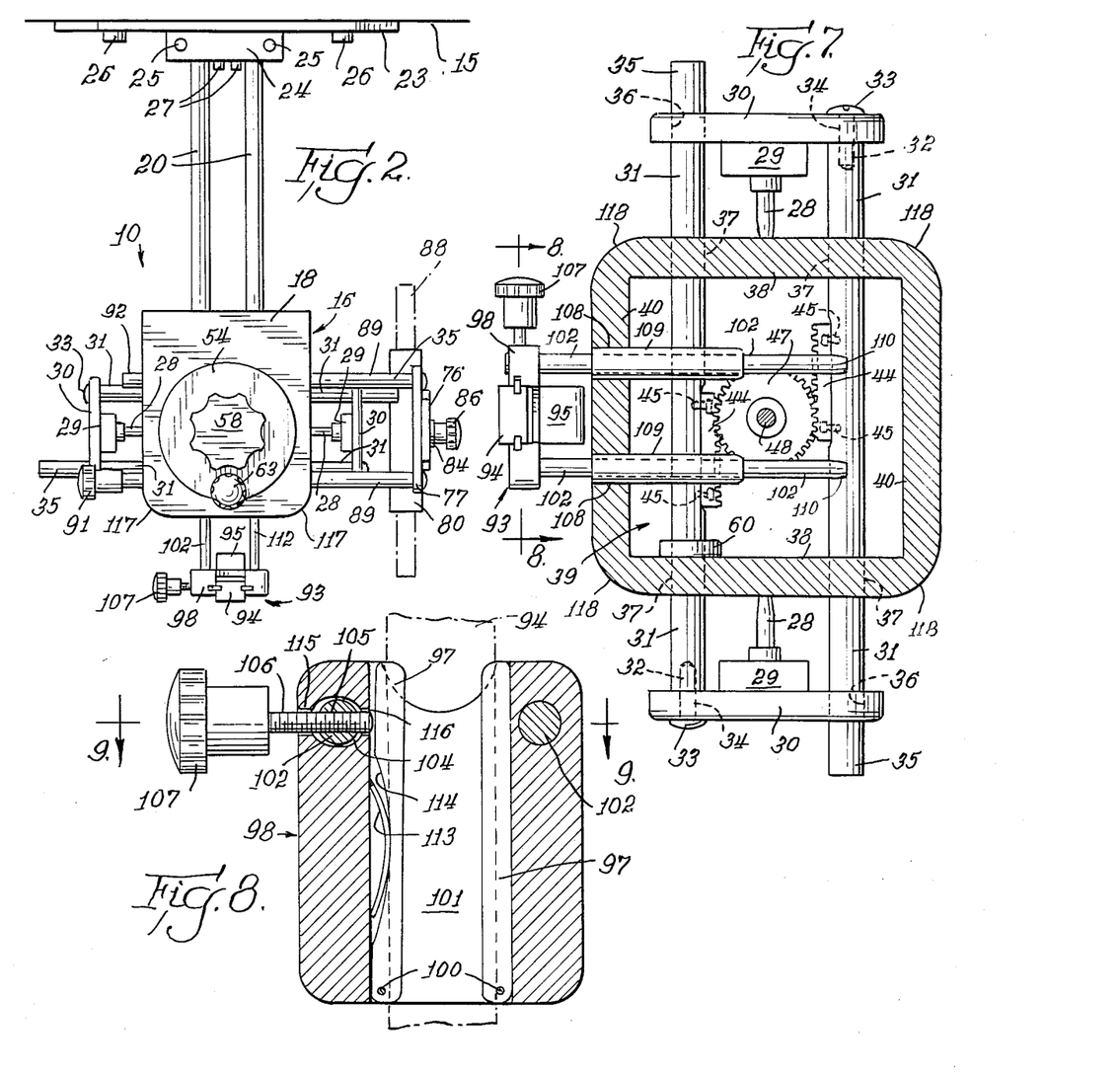
FIG. 2 is a top view of the cephalostat shown in FIG. 1.
FIG. 7 is a horizontal sectional view taken along line 7—7 of FIG. 5, looking in the direction of the arrows, but showing the bottom housing portion indexed 180° relative to the position shown in FIG. 5 for the opposite lateral exposure.
FIG. 8 is a vertical sectional view taken along line 8—8 of FIG. 7, looking in the direction of the arrows, and showing the nasion positioner of the cephalostat; and, FIG. 9 is a horizontal sectional view taken along line 9—9 of FIG. 8, looking to the direction of the arrows, and showing the nasion positioner including a nose slide and guide sleeve means thereof for lateral and vertical adjustment relative to the first and second cephalostat housing portions.
Figure 3:
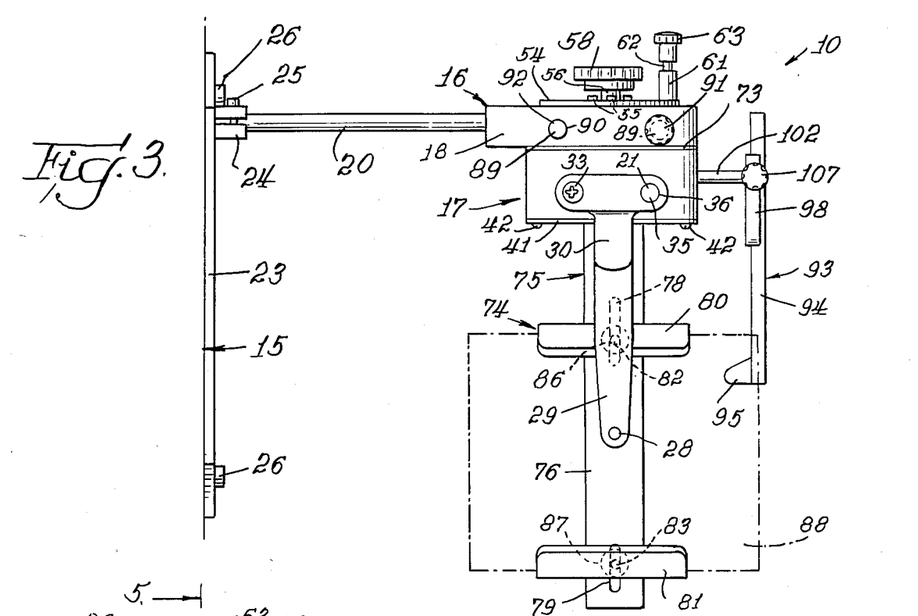
FIG. 3 is a side, elevational view of the cephalostat shown in FIG. 1 taken from the left side thereof.
Figures 4, 9:
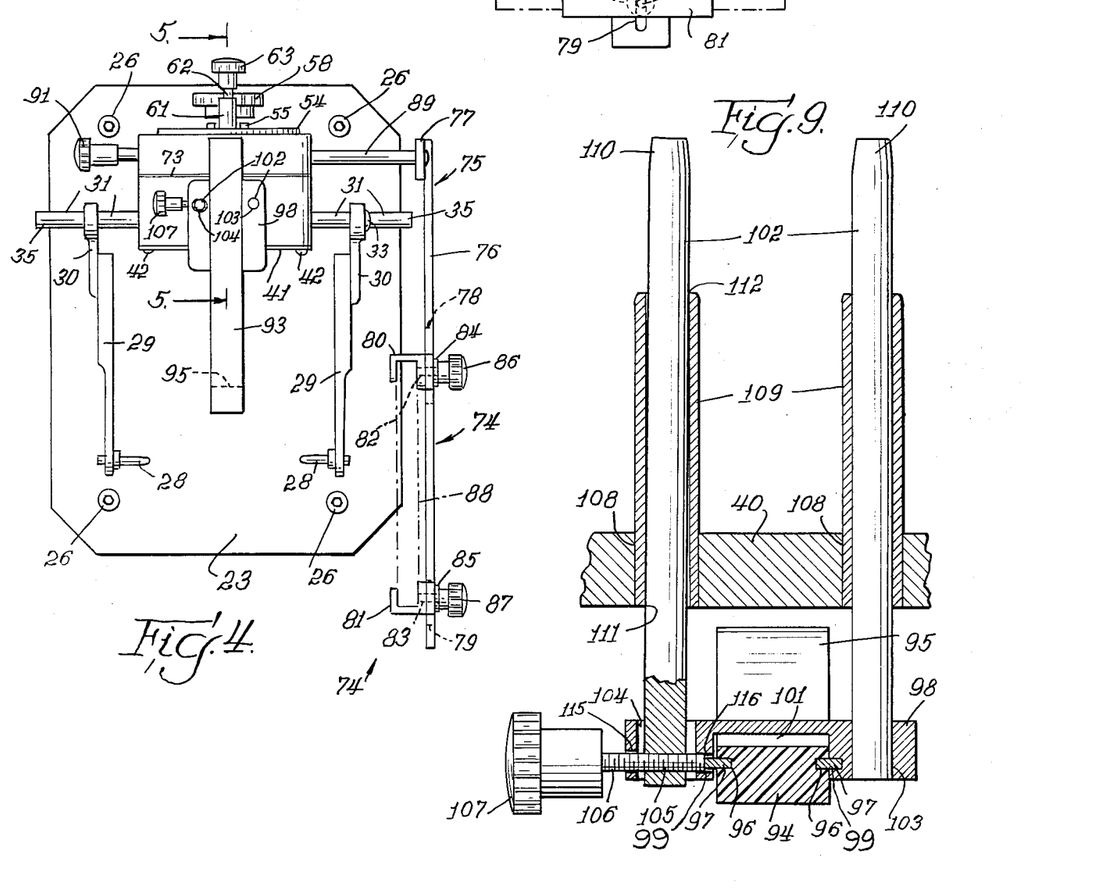

With reference now made to FIGS. 2, 3 and 4, it will be observed that top, left-side, and front views, respectively and with reference to the view shown in FIG. 1, are provided. The improved cephalostat 10 includes a two-housing construction which conveniently and efficiently provides for an adjustable reciprocating earpost assembly, adjustment means for an x-ray film cassette holder, support and adjustment means for a nasion positioner, and the capability whereby one housing may be rotated relatively to the other to provide for lateral, frontal oblique, anterior, and posterior, roentgenography for taking cephalometric series of x-ray pictures over time. Additionally, the improved cephalostat 10 provides for the attachment to demountable support means relative to a wall mounting plate so that the unit may be conveniently stored when not needed whereby to give the dental practitioner spacesaving benefits.

In greater detail, the cephalostat 10 will be seen to have a top, or first housing 16, which is fixed above a relatively movable bottom, or second, housing 17. The top housing 16 includes a rearward-extending, engagement portion 18, which, as best viewed in FIG. 3, extends toward the wall 15 past the bottom housing 17.

Figure 5:
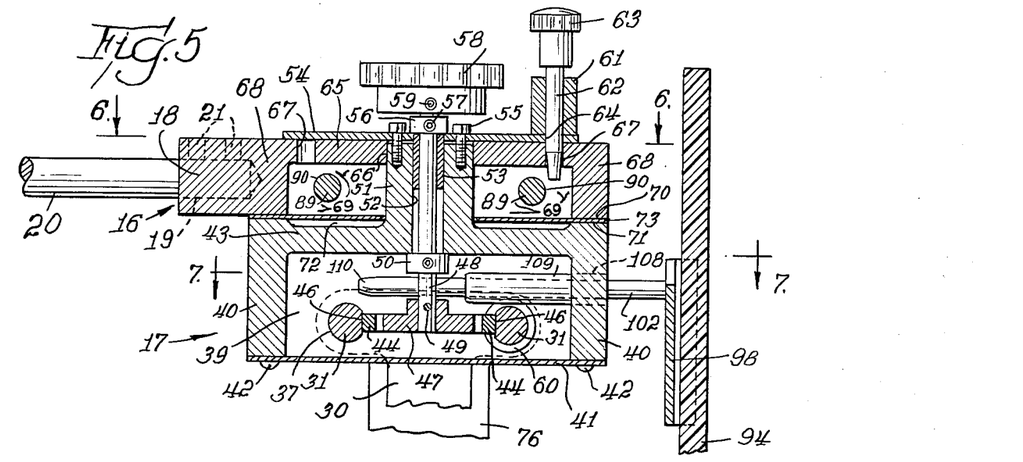
FIG. 5 is a vertical, sectional view of the cephalostat taken along line 5—5 of FIG. 4, looking in the direction of the arrows.

The rearward portion 18 includes a pair of bored-out recesses 19 for the receipt therein of the ends of a pair of parallel support rods 20. With further reference now made to FIG. 5, the cephalostat 10 is shown in vertical section whereby it will be seen that the rearward extending engagement portion 18 further includes two pair of threaded holes 21 extending from the top thereof downwardly to the recesses 19 whereby to provide for the attachment of threaded, set-screw fasteners 22 for securing the support rods 20 within the recesses 19. The location of the set-screw fasteners 22 are best viewed in FIG. 6.

The support rods 20 are attached to a wall mounting plate 23 at wall 15 whereby to support the cephalostat 10 at a selected distance away from the wall 15 corresponding to the distance at which the x-ray tube 12 is held by the fixator/collimator 14, as would be clear. The wall mounting plate 23 includes a releasable clamping bracket 24, shown in FIGS. 2 and 3, wherein screw fasteners 25 are utilized to tighten the releasable clamping bracket 24 generally around the ends of the support rods 20. The wall mounting plate 23 is attached to the wall 15 by means of standard screw fasteners 26 extending into the wall 15, preferably into wall studding, or other structural support means within the wall, for the sturdy support of the wall mounting plate 23, support rods 20, and the cephalostat 10.

Accordingly, the release of the screw fasteners 25 permits the cephalostat 10 to be quickly and easily dismounted from the wall 15. The conventonal, articulated arm means 13 of the x-ray apparatus 11 may be also conveniently folded against the wall and the fixated/collimater 14 may be of a known removable design. Thereby, the cephalostat 10 is usable with other such conventional, removable x-ray devices in order to give the dental practitioner a spacesaving benefit.

It will be further seen that the releasable, clamping bracket 24 includes clamp bracket fasteners 27 which affix the clamping bracket 24 to the mounting plate 23. Optionally, these fasteners 27 may be removed instead of fasteners 25 whereby the clamping bracket 24, while attached to the support rods 20, may be removed with the rods 20. The detachment of the fasteners 27, or fasteners 25, are alternate provisions that offer further versatility to the improved cephalostat 10.

The improved cephalostat 10 also includes a pair of opposing earposts 28, which preferably have plastic or wood projections, in a known design, for insertion into the ear canals of the patient for arranging the patient's head in the proper orientation. The earposts 28 are attached to elongated, vertical arms 29, which are also made of preferably wood or plastic, whereby neither the earposts 28 nor the arms 29 will appear on the x-ray picture. Although, small metal holder rings, usually made from brass, may be provided on the earposts 28 in a known design for use as potential reference points on the x-ray image. The arms 29 are supported at the tops thereof by T-shaped brackets 30, best viewed in FIG. 3.

With reference now made to FIG. 7, the adjustment means for the earposts 28, arms 29, and brackets 30, for moving them away from, or toward, the patient's head, when he or she is seated beneath the bottom housing 17, is shown. It will be observed that the T-shaped brackets 39 are inter-connected by a pair of reciprocating parallel support rods 31, extending through the bottom housing 17 as will be explained hereinafter.

One end of each of the rods 31 is provided with a threaded axial-bore 32 having a machine screw 33 thread-engaged therein and passing through holes 34 which extend through the brackets 30. Each of the rods 31 has the other end thereof free, generally shown at 35. The rods 31 are thereby slide-movable through smooth bores 36 also extending through the brackets 30. Thus, each bracket 30 fixably accommodates one end of one rod at the bore 32 and slidably accommodates the other end of the other rod.

The parallel support rods 30 support the T-shaped brackets 30 by means of extending through two pairs of bores 37 made through opposing sidewalls 38 of the bottom housing 17, best viewed in FIG. 5 in conjunction with the horizontal sectional view of FIG. 7. One pair of bores 37 thereby oppose the other and are in parallel axial alignment between the sidewalls 38 in order to maintain the support rods 31 in parallel, slidable relationship relative to, and through, the bottom housing 17. Interiorly of the bottom housing 17, the rods 31 extend through an interior cavity 39 of the housing 17 which is defined by the opposing sidewalls 38 and two transverse integrally-formed opposing sidewalls 40 of housing 17. Cavity 39 is downwardly open. A bottom cover plate 41, shown in FIG. 5, covers the downwardly open interior cavity 39 and is attached to the bottom edges of the walls 38 and 40 by means of screw fasteners 42 removably threaded therein. The cover plate 41 is thereby desirably provided to be removable in order to grant access to the interior cavity 39, which aids in the maintenance, repair, and adjustment, of the improved cephalostat 10, as would be clear to one skilled in the art. The interior cavity 39 is further defined by a top wall 43 of the lower housing 17, which in the exemplary embodiment is also integrally-formed with sidewalls 38 an 40.

The relative spacing adjustment of the earposts 28 will be seen to be accomplished by the reciprocating movement of a pair of opposing gear racks 44 which are affixed to support rods 31 along a portion thereof interiorly of the cavity 39 by means of screw fasteners 45 engaging therebetween. The gear racks 44 nest along flattened sides 46 of the support rods 31 as best viewed in FIGS. 5 and 7. The gear racks 44 are preferably made of brass and are drivingly teeth-engaged by a gear 47 therebetween whereby to be oppositely movable thereby, or reciprocal, upon the rotation of the gear 47. The gear 47 is rotatable by a shaft 44 attached in an axial bore therethrough by means of a set screw 49, as illustrated in FIG. 5. Along the shaft 48 a limit-stop collar 50 is arranged to be abutted against the underside of the top wall 43 of the interior cavity 39, but is not affixed to wall 43 so that it is rotatable generally thereagainst. The limit-stop collar 50 thus rotatably abuts against the wall 43 and as a result, spaces the gear 47 to be in sure geartooth engagement with the gear racks 44 by preventing gear 47 from moving up from the same horizontal plane as gear racks 44, as would be clear. Downward limitstop means for the gear 47 will be discussed hereafter.

The bottom housing 17 is formed with an upstanding hub 51 extending from the topside of the top wall 43, and is preferably integrally formed with the wall 43. The hub 51 has a center axial bore 52 axially aligned with gear 47 for the rotatable accommodation therein of the shaft 48. The center bore 52 will be seen to have a greater diameter than the shaft 48, as best viewed in FIG. 5. Located near the top and generally in the upper half of the bore 52, a bushing sleeve 43 is press-fit therein and has an inside diameter just slightly larger than that of the shaft 48 whereby to generally hold and center the rotatable shaft 48. The bushing sleeeve 53 preferably does not extend for the full length of the center bore 52 in order to permit a small amount of relative movement of the shaft 48 within the center bore 52, and also thereby allow for slight machine tolerance differences by providing for a compensatory motion whereby to prevent binding and allow for possible slight mis-machining.

The shaft 48 extends outwardly from the center bore 52 and is surrounded by an indexing plate 54 which has a central opening therethrough freely accommodating the bushing sleeve 53 with the shaft 48 therein. The indexing plate 54 is secured to the top of the hub 51 by means of machine screw fastener and washer means 55 extending into the hub 51, which is most clearly understood with reference to the sectional view of FIG. 6 taken generally along a horizontal plane passing just below the indexing plate 54. A second limit-stop collar 56 is secured around the shaft 48 by means of a set screw 57 and is located generally in rotatable abutting contact against the bushing sleeve 53 and partly against the surrounding indexing plate 54, as shown in FIG. 5. Thereby, the vertical movement of the shaft 48 is limited upwardly and downwardly by the stop-collars 50 and 56 respectively, whereby to maintain the gear 47 in generally the same horizontal plane as the gear racks 44 for sure gear tooth engagement therebetween.

The adjustable and reciprocal movement of the support rods 31 and thereby the earposts 28 will therefore be seen to be accomplished by the rotation of the gear 47 which moves the gear racks 44 in opposite directions for the relative positioning of the earposts 28 closer together, or further apart, during the positioning of the patient below the housing 17. The movement of the support rods 31 is made by manually turning a top adjustment knob 58 secured to the shaft 48 above the limit stop collar 56 by means of a set-screw 59. The top adjustment knob 58 is thus provided to be generally centrally located above the top housing 16 in a convenient and efficient location that allows the dental practitioner to position the patient's head and simply reach atop the housing 16 for turning the top adjustment knob 58 to thereby move the earposts 28 to proper placement with the ear canals. This adjustment is thus simply performed to help assure patient confidence, and to allay any potential fears, since the procedure may be accomplished very quickly and with the physician maintaining face-to-face contact for any required communication with the patient.

In order to prevent the lateral disengagement of the gear 47 from the gear racks 44, should knob 58 be roughly, or inadvertently, turned too far in the counterclockwise direction, as viewed in FIG. 7, a horizontal limit stop-collar 60 is loosely arranged along one of the support rods 31 between one of the gear rack 44 and the sidewall 38. The gear racks 44 associated therewith can therefore move no closer to the wall 38 than the thickness of the limit stop 60. Thus, the outward travel distance of the gear racks 44 is defined by the thickness of the limit stop collar 60 at which point the last gear teeth of the gear racks 44 will be maintained in gear-tooth engagement with the gear 47 at that end limit position. The opposite, or inward, travel distance is defined by the position at which the T-brackets 30 contact the walls 38, at which point the last gear teeth of gear racks 44, at the opposite ends, will be maintained in gear-tooth engagement with the gear 47.

Figure 6:
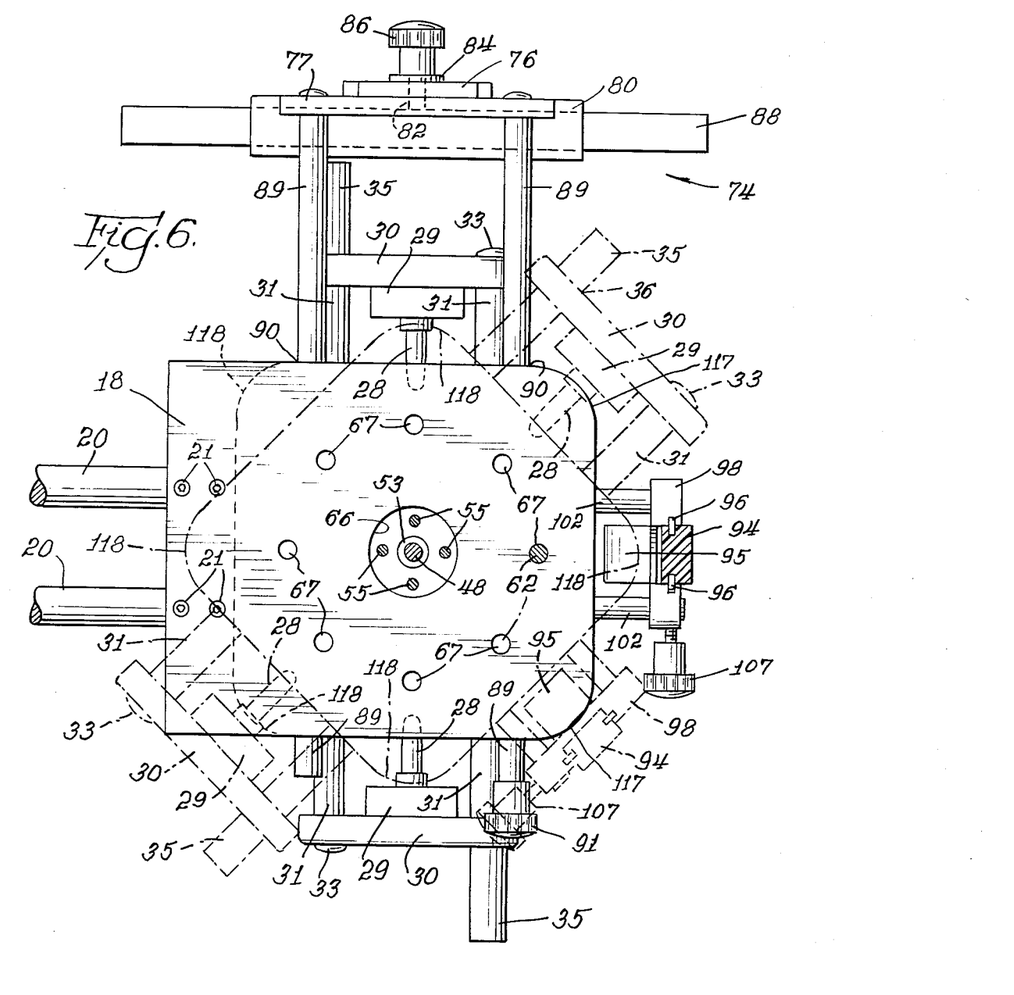
FIG. 6 is a horizontal, sectional view of the cephalostat taken along line 6—6 of FIG. 5, looking in the direction of arrows, and in dashed lines showing a rotational adjustment of the bottom, or second, housing portion relative to the top housing portion for frontal oblique roentgenography.

The function of the indexing plate 54 will now be explained in the achievement of a major purpose of the cephalostat 10 for providing an adjustment of the bottom housing 17 relative to the fixed top housing 16 whereby the patient's head position may be changed from a lateral cephalometric arrangment to anterior, posterior, or oblique, orientations, as will be more clearly understood with reference to FIGS. 5 and 7. An axially bored collar 61 is affixed atop the indexing plate 54, such as by welding, and spaced from the top adjustment knob 58. An indexing pin 62 removably inserts through the collar 61 and includes an upper knob, or handle, 63 which prevents the pin 62 from falling downwardly through the collar 61 and which is provided to be gripped by the dentist or orthodontist for the removal and re-insertion of the indexing pin 62 in order to accomplish the rotational re-positioning of the bottom housing 17, as is described in greater detail herinafter. A hole, or aperture, 64 extends through indexing plate 54 in axial positional correspondence with the collar 61 for the receipt therethrough of pin 62. The upper housing 16 has a top wall 65 upon which the indexing plate 54 is movably arranged as shown in FIG. 5. The top wall 65 includes a center bore 66 for receipt therethrough of the hub 51 of the bottom housing 17. The diameters of the center bore 66 and hub 51 are sized whereby to permit hub 51 to be rotatable therein. The top wall 65 includes a series of indexing holes 67 best viewed in FIG. 6. In the exemplary embodiment there are eight indexing holes 67 spaced equi-angularly therebetween whereby to provide 45° incremental indexing positions. In FIG. 6, shown in dashed lines, the bottom housing is rotated clockwise 45° from the standard right side lateral positioning shown in solid lines, toward the x-ray tube 12 to a frontal oblique position. This is accomplished by the practitioner gripping the knob, or handle, 63 and moving the pin 62 upwardly through the collar 61. Accordingly, the pin 62 is therefore also removed upwardly from engagement with one of the indexing holes 67. The pin 62 need not be fully removed outwardly of the collar 61 as would be clear. Because the indexing plate 54 is secured by the machine screw fastener and washer means 55 to the hub 51 of the bottom housing 17, when the hub 51 is rotated, it carries the indexing plate 54 in the same rotational movement whereby to rotate the plate 54 on the top wall 65 of the upper housing 16 until the next selected index hole 67 is axially aligned beneath the collar 61. At that point the dentist may then push downwardly on the knob 63 to re-insert the pin 62 back through the hole 64 and into the next selected indexing hole 67. The indexing plate 54 preferably is lubricated at the underside thereof whereby to provide for a smooth rotational movement on the surface of the top wall 65.

Extending downwardly from the top wall 65 is a peripheral sidewall 68 of the housing 16 that is preferably integrally formed with top wall 65. It will observed that the sidewall 68 generally forms the lateral wall structure for housing 16, and includes, at the rear side thereof facing wall 15, the rearward extending wall portion 18 having the engageable recesses 19, as explained above. The top wall 65 and the depending sidewall 68 form a cavity 69 within the top housing 16 and in which the hub 51 of the bottom housing 17 extends centrally therethrough, as best depicted in FIG. 5.

The wall 68 has bottom horizontal edge surfaces 70 extending peripherally therearound and which rest atop, in movable relation to, corresponding top horizontal edge surfaces 71 of the top wall 43 of the second housing 17. Further, it will be seen that adjacent the horizontal edge surfaces 71, the top wall 43 includes an indent, or recessed well, portion 72 between the edge 71 and the hub 51 which aids in preventing any imperfections in machining, surface unevenness, or close tolerances, from causing the two housing portions to bind or impede each other during rotation. In order to further facilitate a smooth rotation of the bottom housing 17 relative to the top housing 16 around surfaces 71 and 70, a greased fibre pad 73 is sandwiched therebetween which may include, for example, a white lithium grease well-known to the industry. As a result, a smooth rotation of the housing 17 relative to the housing 16 is quickly and easily accomplished by the removal of the pin 62 upwardly from the indexing hole 67, then the rotation of the bottom housing 17 to the next desired indexed position, and lastly the re-insertion of the pin 62 thereat. It will also be noted that the tip of the pin 62 is tapered whereby it may tightly fit within an indexing hole 67 and also provide an easily inserted configuration for placement within an indexing hole 67. The holes 67 extend fully through the top wall 65 in the exemplary embodiment and therefore the cavity 69 accommodates a portion of the tapered end of the pin 62, as shown in FIG. 5. The index plate 54, pin 62 and index holes 67 cooperate with the housing 17 whereby the pin 62 is spaced to a side of cavity 69, when inserted, and which is efficiently arranged to additionally permit the accommodation of slide support means for a cassette holder within the cavity 69, which will be explained hereinafter.

It is not necessary that the holes 67 extend fully through top wall 43 and they might optionally comprise recessed plug holes having a bottom wall. However, by extending through wall 43, the shank of the pin 62 can be made a little oversized to tightly wedge the tapered end into the index holes 67 for a very rigid, but releasable, lock between the housing portions 16 and 17.

The eight indexing holes 67 are spaced at 45° intervals. However, the indexing holes 67 may be spaced at any desirable interval or arrangement as might be required. As would be clear, a larger or smaller number of holes 67 may be provided. With the various arrangements of pin 62 with holes 67, as shown in FIG. 6, it will be noted that the patient's head may be positioned: laterally with either side of the skull toward x-ray tube 12; posteriorly whereby the back of the head is toward the x-ray tube; 180° anteriorly whereby the front of the head is toward the x-ray tube; or, obliquely whereby the head may be positioned at any of four 45° angular, relationships between anterior/lateral and posterior/lateral made possible by the eight equi-spaced index holes 67.

It will be therefore seen that the improved cephalostat 10 achieves wall-demountability for space saving needs in the dentist's office, as well as locating a top adjustment knob 58 for the earposts conveniently atop the upper housing of the cephalostat 10 to be closely adjacent the adjustable index pin 62 for changing the angular relation of the bottom housing relative to the top housing to provide for the frontal, oblique, anterior, etc. positioning of the patient, all in a very efficient arrangement simply having the two housing portions 16 and 17.

In the disclosed embodiments of cephalostat 10, the housing portions 16 and 17 are machined from aluminum slugs, but in one alternative, they may be cast in a mass production procedure. The machining of the slugs to provide the major features of the hub 51, cavity 39, surface 71 and indents 72 of the lower housing 17, and the surface 70, cavity 69, and the central bore 66 for receipt of the hub 51, of the upper housing 16, do not require detailed bends, bevels and angles. Thus, while of course requiring a workmanlike machining job, the housing 16 and 17 formations are fairly straightforward and may be accomplished without time consuming and burdensome complicated machining procedures.

The improved cephalostat 10, further provides for the adjustability of an x-ray cassette holder relative to the housing 17 as will now be described.

A cassette holder assembly 74, is shown generally throughout the figures. With particular reference to FIGS. 2, 4 and 6 that it will be seen that the cassette holder assembly 74 includes a T-bracket member 75 having a vertical leg 76 and T-cross member 77 forming the arms of the T-shape. The leg 76 includes a top slot 78 spaced from a bottom slot 79, vertically aligned therebelow. The top slot 78 associates with an upper inverted U-shaped holder, or channel, 80 and the bottom slot 79 associates with a lower U-shaped holder, or channel, 81 opening upwardly in opposition to holder 80 whereby to provide opposing channel-like holding means for receiving opposite side edges of an x-ray film cassette. The top holder 80 includes a threaded stud 82 extending therefrom and the bottom U-holder 81 similiarly includes a threaded stud 83. The threaded studs 82 and 83 respectively extend through the slots 78 and 80 and at the other side of the leg 76 have washers 84 and 85, respectively, arranged therewith. An upper lock knob 86 thread engages with the stud 82 whereby to be able to tighten and loosen the washer 84 against the leg 76. A bottom lock knob 87 thread engages stud 83 and, similarly, may loosen and tighten the washer 85 against the leg 76. Thereby, it will be seen that the top and bottom U-holders 80, 81 may be vertically moved after loosening the lock knobs 86, 87, and thereafter tightening them at a desired spacing for holders 80, 81. An x-ray film cassette 88, shown in dashed lines in FIGS. 2 and 3, has its opposite horizontal frame edges held by the opposingly-faced U-holders 80, 81. In the exemplary embodiment, the top slot 78 is three inches in length, and the bottom slot 79 is two inches in length. Thereby, an x-ray film cassette 88, is able to be held therebetween either lengthwise or sideways, and further, its elevation relative to the patient's skull may be varied whereby to arrange it, or center it, as required, for the roentgenograph. This feature thus gives the practitioner adjustability for use with small children, adults, and for other particular roentgengraphic nuances and details that may be involved in a cephalometric series.

Horizontal adjustable positioning of the x-ray film cassette 88 relative to the bottom housing 17, and thus to the mid-sagital plane of the patient's head, is also made possible by the provision of slide rods 89 supportably carrying the T bracket member 75. The slide rods 89, shown in section FIG. 5, are in parallel arrangement and extend through, and are supported by, bores 90 which are two pair of axially-aligned bores through the wall 68 of the upper housing 16. The bores 90 are formed to be slideably engaged with the slide rods 89. The adjustable positioning of the film cassette 88 relative to the patient's head may be easily achieved by the practitioner gripping a limit-stop knob 91 fixed at the end of the front slide rod 84 that projects outwardly from the other side of the housing 16, as shown best in FIG. 4, and then pushing or pulling on the knob 91 to thereby correspondingly slide the associated slide rod 89. The T bracket member 75, affixed to other slide rod 89, both then move together as a unit relative to the housing 16. The other, or back, slide rod 89 has a free end 92, best viewed in FIGS. 3 and 6, which is prevented from sliding inwardly of the cavity 69 by the limit-stop knob 91 attached to the front slide rod 84. Therefore, it will be understood that the lengths of the slide rods 89 are substantially the same. For convenience and ease of use, it is the said frontmost slide rod 89 which has the limit-stop knob 91 to thereby dispose it closely to the practitioner's hands as the patient is being positioned below. It will also be seen from FIG. 4 in conjunction with FIG. 3, that the location of the limit-stop knob 91 is also conveniently arranged near the top adjustment knob 58 and index pin knob 63, to allow quick and sure adjustment and positioning of all.

The cavity 69 of the upper housing 16 is cooperative to accommodate therein the slide rods 89 of the cassette holder assembly 74, as well as cooperatively accomodating the insertion of the tip portion of the pin 62 as it is positioned into various arrangements with the indexing holes 67.

The fixed, upper housing 16 supportably assists the cassette holding assembly 74 to be securely positioned relative to the patient's head, which may be oriented in various angular relationships to the film cassette 88 by virtue of the rotational adjustments of the movable bottom housing 17. It will also be appreciated that the distance between the x-ray film cassette 88 and upper housing 16 may be required to be set at a pre-selected distance for a given cephalometric series so that the distance between the x-ray tube 12 and cassette 88 achieves an exposure image desired by the orthodontist. Thus, for example, a longitudinal sleeve, cut to a set length, may be arranged over one of the slide rods 89, whereby the cross portion 77 of the T-shaped bracket member 75 would be moved to abut the sleeve at this set distance from the sidewall 68 of the housing 16. Also, for example, a flexible plastic tube may be cut to 1-inch, 2-inch, and 3-inch lengths, then slit lengthwise, and then one may be selectively placed around one of the slide rods 89, so that the cross member 77 may then be moved toward the housing 16 and stopped by the specific length of tubing chosen. Accordingly, the tubing would be required to be slightly larger than the bores 90 through the walls 68, so that the tubing would not inadvertently be pushed to enter them. It is known to mark, or calibrate, slides for cassette holders by manufacturing them with a scale, or the like. However, it is one purpose of the present invention to reduce manufacturing costs without sacrificing precision. For cephalostat 10, the individual practitioner can easily and precisely calibrate the cassette holder assembly 74 to suit individual exposure distance specifications, such as by means of the foregoing example of a cut sleeve. Other calibrating means will be clear to those skilled in the art.

The improved cephalostat 10 also provides for the combination with a nasion positioner apparatus 93 in a cooperative arrangement to provide the cephalostat 10 with versatility, precision and accuracy for efficient use by both the general dental practitioner and the specialist. The invention therefore includes a combination with the nasion positioner assembly 93, which preferably aligns with the mid-sagital of the patient's head, and positions the nasion in the proper horizontal plane, such as is usually required for positioning the Frankfort plane in the standard position relative to the x-ray picture as is known in the dental arts. The nasion positioner assembly 93 includes a preferably clear plastic nose slide 94, having at its lower end a curved positioner for the placement of the nasion, or bridge of the nose, thereagainst. As with the earposts 28 and arms 29, it is desirable that the nose slide 94 and positioner 95 be comprised of wood, plastic, or some other material, which would not appear on, or shadow, the x-ray picture. The nose slide 94 includes longitudinal side slide grooves 96 best viewed in the sectional view shown in FIG. 9. These slide grooves 96 extend along substantially the full length of the nose slide 94 and are sized whereby to receive guide strips 97 along both sides of the slide 94. The guide strips 97 are held by, and preferably have about the same length as, a bracket 98 which holds them in complementarily-shaped receiving grooves 99 at their edges opposite the grooves 96 whereby the nose slide 94 is held therebetween as will be explained. Pins 100, depicted in FIG. 8, secure the guide strips 97 to the bracket 98. The bracket 98 includes a generally central slide channel 101 wherein the nose slide 94 is vertically movable by virtue of the grooves 96 sliding along the guide strips 97. The bracket 98 may be made of aluminum, stainless steel, or other metal, since it is located out of the way of the x-ray beam generally in a horizontally spaced relationship with the lower housing 17. The bracket 98 is in supported movable relationship with lower housing 17 by means of slide rods 102 best viewed in FIG. 5. The slide rods 102, preferably comprise a parallel pair of metal rods wherein one of the slide rods 102 is pressfit into an aperture 103 at one portion of the bracket 98 and to one side of the nose slide 94. The other rod 102 is loosely held in an aperture 104 extending through the bracket 98 at the other side of the nose slide 94, as best viewed in FIG. 8. The end of the rod 102 that is loosely held in aperture 104 includes a threaded tranverse bore hole 105 for threadable receipt therein of a threaded stem 106. The threaded stem 106 extends through the edge of the bracket 98 from the adjacent guide strip 97 through the bore hole 105 and outwardly from the bracket 98 to be fixed to a knob 107 whereby stem 106 may be loosened or tightened by the rotation of the knob 107. The tightening of the knob 107 serves to lock both the rods 102 at a particular position relative to the lower housing 17, and at the same time serves to fix the vertical position of the nose slide 94, as will be described hereinafter.

The bottom housing 17 includes a pair of holes 108 through one of the walls 40 as shown in FIG. 9. The holes 108 support the slide rods 102 and are spaced apart substantially the same distance as the slide rods 102 whereby they may be maintained in parallel arrangement. The slide rods 102 are slidably supported through the holes 108 by pressfit sleeve bushings 109 fit within the holes 108. The sleeve bushings 109 extend inwardly of the cavity 39 of the lower housing 17 for preferably a substantial portion of the length of the slide rods 102 in order to achieve secure support of the rods 102 therein whereby the rods 102 are restrained from undesired pivoting and wherein the nasion positioner assembly 93 is substantially assured of being maintained with the nose slide 94 generally vertical. The slide rods 102 have inward free ends 110 which will be seen to be movable in and out of sleeve bushings 109 within the cavity 39 at either side of the shaft 48 and above the gear 47 and gear racks 44, as best viewed in FIG. 7. Additionally, the sleeve bushings 109 are arranged through the apertures 108 to be cooperatively accomodated above the support rods 31, which carry the earpost brackets 30. Thereby, the slide rods 102 may be moved inwardly and outwardly of the wall 40 with the free ends 110 traveling freely and unimpeded within the cavity 39. The slide rods 102 do not include limit stops, or collars, at the free ends 110 so that the slide rods 102 may be removed outwardly of the wall 40, such as when the nasion positioner assembly 93 needs to be adjusted, or if it is not required in a particular series of roentgenography. In order to lock the rods 102, and the positioner 93, it will be seen that by tightening the knob 107, it draws, or cants, the rod 102 by means of the stem 106 thread engaging the threaded hole 105 to bind the rod 102 at points 111 and 112, generally at opposite ends of the associated sleeve bushing 109, best viewed in FIG. 9. Thus, the knob 107 serves to slightly take the rods 102 out of parallel relationship whereby a releasable mechanical binding at 111 and 112 serves to horizontally fix the nose slide 94 at a selected distance for the particular patient. At the same time, the tightening of the knob 107 moves the threaded stem 106 against the adjacent guide strip 97 which pushes the guide strip 97 against the nose slide 94 to thereby press the nose slide 94 against the other guide strip 97 in the opposite side groove 96. Thus the opposite guide strip is pressed against the opposite receiving groove 99 of the bracket 98. The nose slide 94 is thereby releasably locked in place. As a result, the nose slide 94 may be first vertically moved to locate the positioner 95 at the appropriate elevation relative to the nasion and then releasably locked thereat by tightening the knob 107, as explained. When the knob 107 is untightened, the nose slide 94 can be prevented from falling downwardly and out of the receiving grooves 99 by the optional provision of a leaf spring 113 arranged within one of the receiving grooves 99 at one side of the bracket 98, as shown in FIG. 8. The associating guide strip 97 preferably has a conforming cut-out recess 114 for accommodating the bowed shape of the leaf spring 113. The provision of the leaf spring 113 is shown at the left side groove 99 with reference to FIG. 8, but could be alternatively provided at the opposite, or right side, receiving groove 99 at the other side of the bracket 98.

It will be observed that the bracket 98 includes two axially aligned bore holes 115 and 116, extending therethrough into opposite sides of the aperture 104 and which axially align with the threaded hole 105 of the rod 102 for the receipt therethrough of the threaded stem 106. The aligned bore holes 115 and 116 may, but need not, be threadably engaged by the stem 106 and the stem 106 thus need only thread engage the threaded hole 105 of the associating slide rod 102, as is shown in FIG. 8. The bore hole 116 extends from apperture 104 and opens to the receiving groove 99 adjacent thereto. The stem 106 passes through the bore hole 116 to be tightened against the guide strip 97, as explained above, in order to releasably lock the nose slide 94. The bore hole 115 extends from aperture 104 and opens outwardly of the bracket 98 for passage of the stem 106 to the knob 107.

With reference to FIGS. 2, 6 and 7, the first housing 16, at side wall 68, preferably has two rounded, frontward corners 117 which are complementarily shaped with four matching rounded corners 118 of lower housing 17 formed at the joinder of the side walls 40 and 38 thereof. Thereby, a symmetric smooth round-corner exterior may be obtained for the cephalostat 10 when used in the anterior, posterior or lateral arrangements of the bottom housing 17 relative to the top housing 16. Additionally, the rounding of the corners at 117 and 118 allows the rotation of the nasion positioner assembly 93 to be freely made so that the nasion positioner assembly 93 need not be re-adjusted outwardly to provide for turning clearance. Thus, the complementarily shaped rounded corners 117 and 118 permit the dentist or orthodontist to keep the nasion positioner assembly 93 in one position during rotational adjustments of the housing 17 relative to housing 16 for an expeditious and precise roentgenography series in the various angular positions of the skull relative to the x-ray tube 12 that are made possible by the invention.

It will be clear to those skilled in the dental arts that the lower housing 17 efficiently provides for the adjustment of the nasion positioner assembly 93 both horizontally and vertically while, at the same time, cooperatively accommodating the gear 47, racks 44, shaft 48 and rods 31 which provide the means for adjusting the relative movement of earposts 28. Moreover, the lower housing 17 also cooperatively includes the hub 51 extending therefrom whereby to be rotatable relative to the fixed upper housing 16 by carrying thereon the index plate 54 and permitting the index pin 62 to be selectively arranged into indexing holes 67 extending through the top wall 65 of the upper housing 16. The indexing plate 54 is rotatably carried by the hub 51, and the hub 51 provides a central bore 52 for the cooperative rotation of the shaft 48 therein effected by means of turning the conveniently located top adjustment knob 58 centrally positioned thereabove. The index pin 62 and the associated adjustment upper knob handle 63 are also conveniently spaced closely to the top adjustment knob 58. In efficient combination with the knobs 63 and 58, the limit stop knob 91 is provided to be also closely positioned thereto, on the frontmost slide rod 89, to adjust the relative positioning of the cassette holder assembly 74 relative to the upper housing 16. The upper housing 16 further may provide the engageable recesses 19 at a extending wall portion 18 whereby to be engaged by support rods 20 that conveniently may be demountably engaged at the other ends thereof with the wall mounting plate 23. However, the invention is not limited to wall mounting for the cephalostat 10 and it is envisioned that the cephalostat 10 may be employed in counter-balanced and mobile devices where the x-ray tube is supported by one arm means and the cephalostat is supported by a second arm means. The downwardly open cavity 39 of the lower housing 17 may be simply covered by a removable cover plate 41 allowing for ease of access interiorly of the cavity 39 for the adjustment and maintenance of the working mechanisms therein. The lubricated fibre pad 73, arranged between the upper and lower housings for the smooth rotational movement therebetween, may be easily re-lubricated since the facile detachment of the top adjustment knob 58, collar 56, and the machine screw and washer assemblies 55, will conveniently release the bottom housing 17 from the upper housing 16 to expose the pad 73, and also allow for further service, maintenance or re-adjustment interiorly of housing 16. The upper housing 16 includes in the cavity 69 the slide rods 89 supporting the cassette holder assembly 74 and also provides a cooperative arrangement for the insertion of the indexing pin 62 as it is changed from one hole 67 to another for the taking of different x-ray pictures of the patient's head including the described adjustments for anterior, posterior, lateral and frontal oblique cephalometric series. Accordingly, the simple two-housing cephalostat 10 provides significant improvements in the art of cephalometric roentgenography and affords substantially all of the capabilities of much more elaborate and costly systems, while providing the necessary precision, and accuracy, with quick adjustments, described herein.

It is envisioned that a broad range of equivalents fall within the scope of the invention and the ambit of the claims appended hereto.

What is claimed is:

1. In a cephalostat of the type that is wall mounted and spaced from an x-ray tube for the taking of a cephalometric series of x-rays in roentgenography and having earpost means for positioning the patient's head between x-ray film held in x-ray film holding means and an x-ray tube apparatus, the improvement comprising;

a cephalostat having two housings, a first housing being fixedly attached by support means to a wall mounting means, and including a top wall means and a first interior cavity means below said top wall means, and the second housing being rotatable relative to the first housing, the second housing including a second interior cavity means and a hub means extending through the first housing and being rotatably supported therewith for relative rotation between and first and second housings;

a gear and gear rack means housed within the second cavity means and movably associating with support means for the earpost means, the gear and gear rack means being capable of moving the support means and the earpost means, and a shaft means rotatably connected to said gear and extending upwardly from said second cavity means through said hub means to be disposed outwardly of said top wall means of the first housing for manual rotational adjustment of said shaft means above said first housing;

indexing means capable of releasably locking said second housing at different rotational relationships with the first housing, said indexing means includes an index pin means extending through an indexing plate means, the index plate means being attached to the second housing and rotatably arranged atop the the top wall means of said first housing, the index plate means including an aperture said index pin means capable of engaging any one of a plurality of index hole means on the top wall means, the index hole means being arranged in spaced relationship along a circular path, said index pin means capable of being selectively inserted into any one of said index hole means through the index plate aperture for releasably locking said second housing at selected rotational relationships relative to said first housing; and support means supported by said first housing and extending within said first cavity means and extending outwardly of said first housing, the support means supporting an x-ray film holding means to be spaced from said first housing, the support means being movable through said first cavity means and being capable of adjustably positioning said x-ray film holding means at different spacings from the first housing.

2. The improvement as claimed in claim 1 wherein said second housing further includes slide rod means extending through wall means thereof and interiorly of said second cavity means, the slide rod means supporting outwardly of said second housing a nasion positioning means wherein said nasion positioning means is horizontally movable by sliding movement of said slide rod means.

3. The improvement as in claim 1 wherein said index hole means open into said first cavity means and wherein the index pin means when inserted through any said index hole means is capable of extending partially into said first means cavity and spaced from said support means for said x-ray film holding means.

4. The improvement as claimed in claim 1 wherein said x-ray film holding means comprises a bracket means supported by said support means and having a pair of slots, a pair of x-ray film cassette holders movably arranged with the slots, wherein the holders may be moved relative to each other for varying the spacing therebetween.

5. The improvement as claimed in claim 1 wherein said second cavity means is downwardly open.

6. The improvement as claimed in claim 1 wherein said first cavity means is downwardly open.

7. The improvement as claimed in claim 1 wherein said support means attaching said first housing to a wall mounting means is demountable from said wall mounting means, said cephalostat capable of being removed therefrom.

8. The improvement as claimed in claim 1 wherein said shaft means connected to said gear means include stop limit means whereby said gear is prevented from disengaging with said gear rack means by said limit stop means.

9. The improvement as claimed in claim 1 wherein the first and second housings include opposingly-faced surfaces formed along wall means of each housing and separated by a lubricated pad means therebetween and enabling a smooth rotation of said second housing relative to said first housing.

10. An improved cephalostat comprising a double housing wherein a first upper housing is fixed and a second lower housing is arranged below the first in rotational relationship with respect to said first upper housing and wherein said upper housing accommodates slideable support means for supportively carrying an x-ray film cassette holder relative to said upper housing and said lower housing includes cavity means housing a gear and gear racks, said gear racks being opposingly mounted to two parallel support rod means extending outwardly of said lower housing and each said support rod means being fixedly connected at one end with an earpost-carrying member, a rotatable shaft means for driving said gear extends from said gear upwardly through both said housings to project above said upper housing for manual rotation, wherein upon the movement of said gear racks in opposing directions, said earposts may be moved toward, or away from, each other, said lower housing and cavity means accommodate slideable slide rod means supportably carrying a nasion positioner laterally of the lower housing, and wherein said slide rod means extend into the cavity means to be spaced from said support rod means for said earposts, the support rod means and slide rod means being independently movable without impeding the movement of the other and wherein said lower housing includes a hub portion extending upwardly through a cavity means of the upper housing, the hub portion being attached to an indexing plate means rotatably resting upon the upper housing, said hub portion and indexing plate means being rotatable together relative to the upper housing, and the hub portion further includes a center bore rotatably housing a shaft means connected to the gear means, the shaft means extending freely through said index plate means and including thereabove a knob means attached to said shaft, the gear means capable of being manually turned to adjust the position of the earpost-carrying members, and wherein the shaft means is freely rotatable independently of the rotation of said lower housing relative to the upper housing.

11. The improved cephalostat as claimed in claim 10 wherein the indexing plate means includes an aperture means and a cooperatively insertable index pin therefor, and wherein the upper housing includes an upper wall having a plurality of index holes spaced at substantially the same radius as the aperture means of the index plate means, said lower housing capable of being rotated to arrange the aperture means of said index plate means selectively over any one of the index holes of the upper wall of the upper housing, wherein the index pin may be inserted through the aperture means and into a selected index hole to facilitate the releasable locking of the lower housing relative to the upper housing at selected rotational orientations thereto.

12. The improved cephalostat as claimed in claim 11 wherein said upper housing includes an outwardly projecting portion, said outwardly projecting portion having engagement means for the engagement thereat of support rod means, the support rod means engaging the upper housing at said engagement means and extending therefrom to be supportively engaged with a wall mounting means for the fixed support of the upper housing.

13. The improved cephalostat as claimed in claim 14 wherein said support rod means is demountably engaged to said wall mounting means.

14. The improved cephalostat as claimed in claim 11 where said slidable support means for said x-ray cassette holder includes limit stop means preventing the slidable support means from disengaging with the upper housing.

15. The improved cephalostat as claimed in claim 11 wherein said x-ray film cassette holder includes a bracket member having cassette-holding means being adjustable in the vertical direction.

16. The improved cephalostat as claimed in claim 15 wherein said cassette-holding means associate with a releasable lock means for adjustably locking the holding means at selected vertical positions on the brackent member.

17. The improved cephalostat as claimed in claim 11 wherein the slide rod means for the nasion positioner are slide engeable within bushing sleeve means, the busing sleeve means extending through wall means of the lower housing and into said cavity means.

18. The improved cephalostat as claimed in claim 17 wherein said nasion positioner includes releasable locking means capable of securing said slide rod means with said bushing sleeve means for adjustably positioning the nasion positioner at selected distances away from said lower housing.

19. The improved cephalostat as claimed in claim 11 wherein said nasion positioner includes a slide means having a nasion contact portion for contact with the bridge of the patient's nose, said slide means being vertically adjustable.

20. In combination x-ray film holding means and a cephalostat apparatus, the cephalostat apparatus comprising: an upper housing having an interior cavity means and an upper wall having a central bore; a lower housing having a side wall and an upper wall, and a central hub portion extending from the upper wall of the lower housing through the central bore of the upper wall of the upper housing and being rotatable within the central bore of the upper housing, enabling the lower housing to rotate with respect to the upper housing; said hub portion further including a central bore through the hub portion and having shaft means rotatably accommodated within the central bore of the hub portion, a gear being affixed at a lower end of the shaft means and opposite sides of the gear are engaged with gear racks for facilitating movement of the gear racks upon rotating of the shaft means, said shaft means extending outwardly of the central bore of the hub portion to extend outwardly above said upper wall of the upper housing and the shaft means being engaged by means for the manual rotation thereof above said upper housing; index plate means movably positioned on the upper wall of said upper housing and being secured to the hub portion of said lower housing to be rotatably supported therewith, wherein said shaft means is rotatable independently of the rotation of said lower housing, and wherein said gear racks are carried on slide rod means extending outwardly of the lower housing, the slide rod means being secured to earpost means sidewardly of the lower housing and being movable toward, or away from, each other dependent upon the direction of the rotation of the gear.

21. In combination x-ray film holding means and a cephalostat apparatus, the cephalostat apparatus comprising: an upper housing having an interior cavity means and an upper wall having a central bore; a lower housing having a side wall and an upper wall, and a central hub portion extending from the upper wall of the lower housing through the central bore of the upper wall of the upper housing and being rotatable within the central bore of the upper housing, enabling the lower housing to rotate with respect to the upper housing; said hub portion further including a central bore therethrough having shaft means rotatably accommodated within the central bore of the hub portion, a gear being affixed at a lower end of the shaft means and engaged at opposite sides thereof with gear racks for facilitating movement of the gear racks upon rotating of the shaft means, said shaft means extending outwardly of the central bore of the hub portion to extend outwardly above said upper wall of the upper housing and being engaged thereat by means for the manual rotation thereof above said upper housing; index plate means movably positioned on the upper wall of said upper housing and being secured to the hub portion of said lower housing to be rotatably supported therewith, wherein said shaft means is rotatable independently of the rotation of said lower housing, and wherein the index plate means associates with the index pin means for releasably locking the index plate means to the upper wall of the upper housing.

22. In combination x-ray film holding means and a cephalostat apparatus, the cephalostat apparatus comprising: an upper housing having an interior cavity means and an upper wall having a central bore; a lower housing having a side wall and an upper wall, and a central hub portion extending from the upper wall of the lower housing through the central bore of the upper wall of the upper hosing and being rotatable within the central bore of the upper housing, enabling the lower housing to rotate with respect to the upper housing; said hub portion further including a central bore therethrough having shaft means rotatably accommodated within the central bore of the hub portion, a gear being affixed at a lower end of the shaft means and engaged at opposite sides thereof with gear racks for facilitating movement of the gear racks upon rotating of the shaft means, said shaft means extending outwardly of the central bore of the hub portion to extend outwardly above said upper wall of the upper housing and being engaged thereat by means for the manual rotation thereof above said upper housing; index plate means movably positioned on the upper wall of said upper housing and being secured to the hub portion of said lower housing to be rotatably supported therewith, wherein said shaft means is rotatable independently of the rotation of said lower housing, and wherein said lower housing includes a slide rod means extending through the side wall of said lower housing and carrying outwardly of the lower housing a nasion positioning means, the slide rod means being independently movable of, and freely spaced from, the gear, gear racks and shaft means.

23. A cephalostat apparatus, comprising, in combination: an upper housing having an interior cavity means and an upper wall having a central bore; a lower housing having a side wall and an upper wall, and a central hub portion extending from the upper wall of the lower housing through the central bore of the upper wall of the upper housing and being rotatable within the central bore of the upper housing, enabling the lower housing to rotate with respect to the upper housing; said hub portion further including a central bore therethrough having shaft means rotatably accommodated within the central bore of the hub portion, a gear being affixed at a lower end of the shaft means and engaged at opposite sides thereof with gear racks for facilitating movement of the gear racks upon rotating of the shaft means, said shaft means extending outwardly of the central bore of the hub portion to extend outwardly above said upper wall of the upper housing and being engaged thereat by means for the manual rotation thereof above said upper housing; index plate means movably positioned on the upper wall of said upper housing and being secured to the hub portion of said lower housing to be rotatably supported therewith, wherein said shaft means is rotatable independently of the rotation of said lower housing, and wherein the cavity means of the upper housing slidably accommodates a pair of slide rod means extending outwardly of the upper housing, said slide rod means being secured to and carried sidewardly of the upper housing an x-ray cassette holding means, wherein the slide rod means being slide-movable for positioning the x-ray cassette holding means at variable distances from the upper housing.

24. In combination x-ray film holding means and a cephalostat apparatus, the cephalostat apparatus comprising: an upper housing having an interior cavity means and an upper wall having a central bore; a lower housing having a side wall and an upper wall, and a central hub portion extending from the upper wall of the lower housing through the central bore of the upper wall of the upper housing and being rotatable within the central bore of the upper housing, enabling the lower housing to rotate with respect to the upper housing; said hub portion further including a central bore therethrough having shaft means rotatably accommodated within the central bore of the hub portion, a gear being affixed at a lower end of the shaft means and engaged at opposite sides thereof with gear racks for facilitating movement of the gear racks upon rotating of the shaft means, said shaft means extending outwardly of the central bore of the hub portion to extend outwardly above said upper wall of the upper housing and being engaged thereat by means for the manual rotation thereof above said upper housing; index plate means movably positioned on the upper wall of said upper housing and being secured to the hub portion of said lower housing to be rotatably supported therewith, wherein said shaft means is rotatable independently of the rotation of said lower housing, and wherein said upper housing further includes engagement means engaged by support means, said support means extending from said upper housing and being secured to a wall mounting means, and wherein the upper and lower housings are supported by said support means.

* * * * *

UNITED STATES PATENT AND TRADEMARK OFFICE
CERTIFICATE OF CORRECTION

PATENT NO. : 4,760,591
DATED : July 26, 1988
INVENTOR(S) : James L. Gallop and Andrew J. Majka It is certified that error appears in the above-identified patent and that said Letters Patent are hereby corrected as shown below:

Col. 16, Line 46 immediately after the word "aperture" insert --,--.

Col. 17, Line 44 immedately before the word "upper" insert --first--.

Col. 18: Line 5 delete "thereabove a"; Line 25 delete the number "11" and insert therefor --10--; Line 34 delete the number "14" and insert therefor --12--; Line 37 delete the number "11" and insert therefor --10--; Line 42 delete the number "11" and insert therefor --10--; Line 51 delete the number "11" and insert therefor --10--; and Line 62 delete the number "11" and insert therefor --10--.

Col. 19: Line 41 delete "therethrough" and insert therefor --through the hub portion and--; Line 44 delete "engaged at"; Line 45 delete "thereof" and insert therefor --of the gear are engaged--; Line 49 immediately before the word "being" insert --the shaft means--; Line 50 delete the word "thereat"; and Line 67 delete the misspelling "hosing" and insert therefor --housing--.

Col. 20: Line 2 delete "therethrough" and insert therefor --through the hub portion and--; Line 5 delete "engaged at"; Line 6 delete "thereof" and insert therefor --of the gear are engaged--;Line 10 immediately before the word "being" insert --the shaft means--; Line 11 delete "thereat"; Line 33 delete "therethrough" and insert therefor --through the hub portion and--; Line 36 delete "engaged at"; Line 37 delete "thereof" and insert therefor --of the gear are engaged--; Line 41 immediately before the word "being" insert --the shaft means--, and delete "thereat"; and Line 66 delete "therethrough" and insert therefor --through the hub portion and--.

UNITED STATES PATENT AND TRADEMARK OFFICE
CERTIFICATE OF CORRECTION

PATENT NO.  : 4,760,591

DATED       : July 26, 1988

INVENTOR(S) : James L. Gallop and Andrew J. Majka

Page 2 of 2

It is certified that error appears in the above-identified patent and that said Letters Patent is hereby corrected as shown below:

Col. 21: Line 1 delete "engaged at"; Line 2 delete "thereof" and insert therefor --of the gear are engaged--; Line 6 immediately befor the word "being" insert --the shaft means--; and line 7 delete "thereat".

Signed and Sealed this

Eleventh Day of April, 1989

Attest:

DONALD J. QUIGG

*Attesting Officer*

*Commissioner of Patents and Trademarks*